United States Patent
Dos Santos et al.

(10) Patent No.: US 10,779,905 B2
(45) Date of Patent: Sep. 22, 2020

(54) FOCUSING OPTICS FOR MIXED MODE SURGICAL LASER ILLUMINATION

(71) Applicant: Novartis AG, Basel (CH)

(72) Inventors: Cesario Dos Santos, Newport Beach, CA (US); Gerald David Bacher, Carlsbad, CA (US); Ronald Smith, Irvine, CA (US); Alireza Mirsepassi, Irvine, CA (US); Michael Papac, North Tustin, CA (US)

(73) Assignee: Alcon Inc., Fribourg (CH)

( * ) Notice: Subject to any disclaimer, the term of this patent is extended or adjusted under 35 U.S.C. 154(b) by 255 days.

(21) Appl. No.: 15/882,790

(22) Filed: Jan. 29, 2018

(65) Prior Publication Data
US 2018/0214238 A1    Aug. 2, 2018

Related U.S. Application Data (60) Provisional application No. 62/453,769, filed on Feb. 2, 2017.

(51) Int. Cl.
| | | |
|---|---|---|
| *A61B 90/30* | (2016.01) | |
| *A61B 17/02* | (2006.01) | |
| *A61F 9/007* | (2006.01) | |
| *G02B 27/48* | (2006.01) | |
| *A61B 3/00* | (2006.01) | |
| *G02B 21/00* | (2006.01) | |

(52) U.S. Cl.
CPC ............ *A61B 90/30* (2016.02); *A61B 3/0008* (2013.01); *A61B 17/0231* (2013.01); *A61F 9/00736* (2013.01); *G02B 21/0012* (2013.01); *G02B 27/48* (2013.01); *A61B 2090/306* (2016.02)

(58) Field of Classification Search
CPC ..... A61B 90/30; A61B 17/02; A61B 17/0231; A61F 9/007; A61F 9/00736
See application file for complete search history.

(56) References Cited

U.S. PATENT DOCUMENTS

| | | |
|---|---|---|
| 5,395,362 A | 3/1995 | Sacharoff et al. |
| 6,299,307 B1 | 10/2001 | Oltean et al. |
| 7,444,057 B2 | 10/2008 | Dacquay et al. |
| 7,499,624 B2 | 3/2009 | Dacquay et al. |
| 7,959,297 B2 | 6/2011 | Silverstein |
| 8,944,647 B2 | 2/2015 | Bueeler |
| 10,238,543 B2 | 3/2019 | Farley |
| 2003/0229270 A1 | 12/2003 | Suzuki et al. |
| 2004/0151008 A1 | 8/2004 | Artsyukhovich et al. |
| 2005/0027288 A1 | 2/2005 | Oyagi et al. |
| 2005/0248849 A1 | 11/2005 | Urey |
| 2006/0045501 A1 | 3/2006 | Liang |
| 2007/0047059 A1* | 3/2007 | Howard ............ G02B 27/0933 359/277 |

(Continued)

FOREIGN PATENT DOCUMENTS

| | | |
|---|---|---|
| CN | 103799961 A | 5/2014 |
| EP | 2945005 A1 | 11/2015 |

(Continued)

*Primary Examiner* — Christopher J Beccia (57) ABSTRACT

Focusing optics for mode mixing may be used to homogenize different modes in an optical fiber used for surgical illumination. A vibration stage may impart mechanical motion to a condenser lens to generate a homogeneous illumination field from a coherent light source.

16 Claims, 5 Drawing Sheets

(56) References Cited

U.S. PATENT DOCUMENTS

| | | |
|---|---|---|
| 2008/0055698 A1 | 3/2008 | Yurlov |
| 2008/0144148 A1 | 6/2008 | Kusunose et al. |
| 2008/0246919 A1* | 10/2008 | Smith ............... A61B 3/0008 351/213 |
| 2008/0269731 A1 | 10/2008 | Swinger et al. |
| 2009/0059359 A1 | 3/2009 | Nahm et al. |
| 2010/0157622 A1 | 6/2010 | Stocks |
| 2011/0144745 A1 | 6/2011 | Martin et al. |
| 2012/0081786 A1 | 4/2012 | Mizuyama |
| 2012/0203075 A1* | 8/2012 | Horvath ............... A61B 1/07 600/249 |
| 2013/0144278 A1 | 6/2013 | Papac et al. |
| 2013/0150839 A1 | 6/2013 | Smith et al. |
| 2013/0158392 A1 | 6/2013 | Papac et al. |
| 2013/0158393 A1 | 6/2013 | Papac et al. |
| 2013/0338648 A1 | 12/2013 | Hanebuchi et al. |
| 2014/0333978 A1 | 11/2014 | Hereen et al. |
| 2014/0350368 A1 | 11/2014 | Irisawa |
| 2015/0277137 A1 | 10/2015 | Aschwanden |
| 2015/0366443 A1* | 12/2015 | Liolios ............... A61F 9/00821 600/249 |
| 2018/0214018 A1 | 8/2018 | Dos Santos et al. |
| 2018/0214021 A1 | 8/2018 | Dos Santos et al. |
| 2018/0214237 A1 | 8/2018 | Dos Santos et al. |
| 2018/0214238 A1 | 8/2018 | Dos Santos et al. |
| 2018/0214239 A1 | 8/2018 | Dos Santos et al. |

FOREIGN PATENT DOCUMENTS

| | | |
|---|---|---|
| EP | 3035110 A1 | 6/2016 |
| GB | 2467181 | 7/2010 |
| KR | 20110011052 A | 2/2011 |
| WO | 9314432 A2 | 7/1993 |
| WO | WO2012122677 A1 | 9/2012 |
| WO | WO2014053562 A1 | 4/2014 |
| WO | WO2014059552 A1 | 4/2014 |

* cited by examiner

FOCUSING OPTICS FOR MIXED MODE SURGICAL LASER ILLUMINATION

BACKGROUND

Field of the Disclosure

The present disclosure relates to surgical illumination, and more specifically, to focusing optics for mixed mode surgical laser illumination.

Description of the Related Art

In ophthalmology, eye surgery, or ophthalmic surgery, is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus.

Additionally, an illumination source is typically introduced into the fundus to illuminate the area where the surgeon will be working. The illumination source is typically implemented as a surgical tool having an illuminator assembly that also penetrates the sclera and may be combined with other surgical tools. The use of optical fibers transmitting coherent light as illumination sources for surgery is desirable because of the high light intensity provided within very small physical dimensions available with optical fibers.

SUMMARY

The disclosed embodiments of the present disclosure provide focusing optics for mode mixing that may be used to homogenize different modes in an optical fiber used for surgical illumination. A vibration stage may impart mechanical motion to a condenser lens to generate a homogeneous illumination field from a coherent light source.

In one aspect, a disclosed method is for surgical illumination. The method may include projecting first light from a coherent light source into an optical fiber using a condenser lens to focus the first light onto a focal spot at a fiber core of the optical fiber, the first light used for illumination of a patient during a surgery. The method may also include vibrating the condenser lens in a plane perpendicular to a transmission direction of the optical fiber. In the method, the focal spot may be moved over the fiber core to generate second light. The method may also include transmitting the second light from the optical fiber to a second optical fiber that projects the second light onto the patient.

In any of the disclosed embodiments of the method, the surgery is an ophthalmic surgery, and the second optical fiber projects the second light into an eye of the patient, while the method further includes measuring an intensity of the second light from the optical fiber. Based on the intensity measured, the method may include controlling the vibrating to limit movement of the focal spot to the fiber core.

In any of the disclosed embodiments of the method, the coherent light source may be a monochromatic laser.

In any of the disclosed embodiments of the method, the coherent light source may be a plurality of monochromatic lasers combined to generate the first light.

In any of the disclosed embodiments of the method, the method operation of vibrating the condenser lens may further include vibrating the condenser lens using a piezoelectric actuator mechanically coupled to the condenser lens.

In any of the disclosed embodiments of the method, the method operation of vibrating the condenser lens may further include vibrating the condenser lens using an electromagnetic actuator mechanically coupled to the condenser lens.

In any of the disclosed embodiments of the method, the method operation of vibrating the condenser lens may further include vibrating the condenser lens using a mechatronic actuator mechanically coupled to the condenser lens.

In any of the disclosed embodiments of the method, the condenser lens may impart at least one of a reciprocal motion and a circular motion to the focal spot.

In any of the disclosed embodiments of the method, the condenser lens may impart a randomized motion to the focal spot.

In any of the disclosed embodiments of the method, the coherent light source may be a third optical fiber receiving the first light from the coherent light source, while the vibrating stage and the condenser lens may be included in a condenser mode mixer device. The condenser mode mixer device may further include an input optical connector for connection to the third optical fiber, an output optical connector for connection to the optical fiber, and a power source to power the vibrating of the condenser lens. In the method, the condenser lens may vibrate at a frequency greater than 30 Hz.

In another aspect, a disclosed device is for surgical illumination. the device may include a coherent light source for generating first light for illumination of a patient during a surgery. The device may also include a condenser lens for focusing the first light onto a focal spot at a fiber core of an optical fiber. The device may further include a vibration stage for vibrating the condenser lens in a plane perpendicular to a transmission direction of the optical fiber, while the focal spot is moved over the fiber core to generate second light. The device may still further include a second optical fiber receiving the second light from the optical fiber, the second optical fiber projecting the second light onto the patient.

In any of the disclosed embodiments of the device, the surgery may be an ophthalmic surgery, and the second optical fiber may project the second light into an eye of the patient, while the device further includes an optical intensity sensor to measure an intensity of the second light from the optical fiber. In the device, the vibration stage may be controlled based on the intensity measured to limit movement of the focal spot to the fiber core.

In any of the disclosed embodiments of the device, the coherent light source may be a monochromatic laser.

In any of the disclosed embodiments of the device, the coherent light source may be a plurality of monochromatic lasers combined to generate the first light.

In any of the disclosed embodiments of the device, the vibration stage may further include a piezoelectric actuator mechanically coupled to the condenser lens.

In any of the disclosed embodiments of the device, the vibration stage may further include an electromagnetic actuator mechanically coupled to the condenser lens.

In any of the disclosed embodiments of the device, the vibration stage may further include a mechatronic actuator mechanically coupled to the condenser lens.

In any of the disclosed embodiments of the device, the vibration stage may cause the condenser lens to impart at least one of a reciprocal motion and a circular motion to the focal spot.

In any of the disclosed embodiments of the device, the condenser lens may impart a randomized motion to the focal spot.

In any of the disclosed embodiments of the device, the coherent light source may be a third optical fiber receiving the first light from the coherent light source, while the vibrating stage and the condenser lens may be included in a condenser mode mixer device. The condenser mode mixer device may further include an input optical connector for connection to the third optical fiber, an output optical connector for connection between the optical fiber and a fourth optical fiber directly coupled to the second optical fiber, and a power source to power the vibrating of the condenser lens.

In any of the disclosed embodiments of the device, the condenser lens may vibrate at a frequency greater than 30 Hz.

BRIEF DESCRIPTION OF THE DRAWINGS

For a more complete understanding of the present disclosure and its features and advantages, reference is now made to the following description, taken in conjunction with the accompanying drawings, in which.

DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, the use of optical fibers and coherent light sources is desirable for surgical illumination because of the high light intensity provided within the very small physical dimensions of an optical fiber. Although such surgical illumination sources may be used in various medical and surgical applications, one exemplary application is in eye surgery, such as for vitreoretinal surgery.

For vitreoretinal surgery, for example, the illumination source is typically implemented as a surgical tool having an illuminator assembly that penetrates the sclera and may be combined with other surgical tools. At a distal end of the illuminator assembly, a very small diameter optical fiber may be used to project light into the fundus to illuminate surgical procedures performed within the eye. The very small diameter fiber, for example having a fiber core of about 25-100 µm, is typically coupled to an optical fiber that couples proximally to a coherent light source, such as a laser source. Although various types of optical fibers may be used, multi-mode optical fibers may be used to transmit coherent light into the eye for illumination.

However, as coherent light is transmitted through a multi-mode optical fiber, different groups of photons of the coherent light, referred to as "modes", within the fiber may traverse slightly different path lengths. As a result of the different path lengths experienced by different modes within the optical fiber, the modes may constructively and destructively interfere with each other during propagation within the optical fiber. As the different modes exit the optical fiber from a fiber core, an illumination field provided by the exiting light may appear inhomogeneous due to the inter-mode interference. The inter-mode interference may be highly sensitive to temperature, fiber strain, fiber motion, and may generally become quite noticeable to the human eye, since the inhomogeneous illumination field projects an undesired dynamic pattern, instead of a homogeneous illumination field projecting uniform background light. Because the inhomogeneous illumination field appears as different regions of different colored light that may be dynamic, the inhomogeneous illumination field may be poorly suited for surgical illumination.

For example, in vitreoretinal surgery, a clear and unambiguous view of various fine biostructures in the eye is highly desirable to enable a surgeon to operate safely and effectively, which the inhomogeneous illumination field may not provide. In particular, the inhomogeneous illumination field is observed with monochromatic laser sources, or combinations of monochromatic laser sources in some implementations. The monochromatic laser sources may exhibit fewer modes and, thus, a lesser degree of mode mixing within the optical fiber that enables homogenization of the coherent light into a desired homogeneous illumination field. Furthermore, as various surgical tools are designed and implemented, such as endoilluminators or surgical tools with combined illumination, the use of smaller fiber diameters carrying high light intensity becomes increasingly desirable. However, the inter-mode interference issues become increasingly exacerbated as the size (i.e., diameter) of an optical fiber decreases, which may undesirably constrain the use of such compact illumination systems. Also, in surgical illumination applications, a relatively short length of optical fiber is used, such as about 2-3 m in length. Because mode mixing that leads to a more homogeneous illumination field increases with fiber length, shorter optical fibers used in surgical illumination applications may experience insufficient mode mixing that results in the inhomogeneous illumination field. Also, optical fibers comprised of a glass core may exhibit fewer modes and less mode mixing, and may be particularly subject to the inhomogeneous illumination field.

As will be described in further detail, focusing optics for mixed mode surgical laser illumination are disclosed. The focusing optics for mixed mode surgical laser illumination disclosed herein may provide a homogeneous illumination field for surgical illumination using optical fibers to transmit coherent light. The focusing optics for mixed mode surgical laser illumination disclosed herein may be used with relatively short and relatively small diameter optical fibers. The focusing optics for mixed mode surgical laser illumination disclosed herein may be used with optical fibers having a glass core. The focusing optics for mixed mode surgical laser illumination disclosed herein may be implemented at a light source for surgical illumination. The focusing optics for mixed mode surgical laser illumination disclosed herein may be implemented as an optical device that can be coupled to an optical fiber providing surgical illumination from a coherent light source. The focusing optics for mixed mode surgical laser illumination disclosed herein may be used for illumination of a patient's eye during ophthalmic surgery, such as vitreoretinal surgery.

Figure 1:
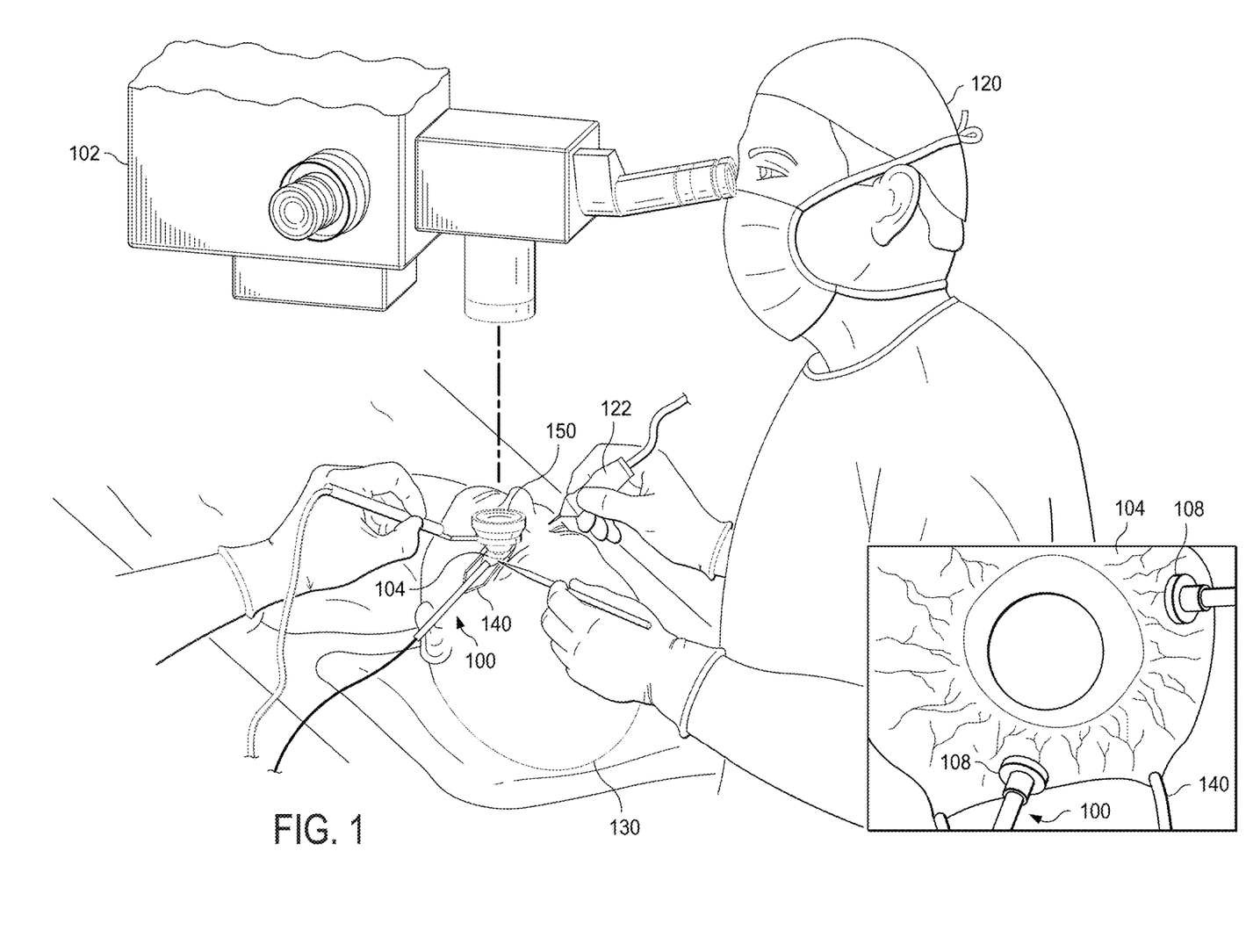
FIG. 1 is a depiction of an embodiment of an ophthalmic surgery using a surgical microscope and a surgical tool with an illuminator assembly.

One manner in which an illumination assembly 100 may be used is illustrated in FIG. 1, in which a surgeon 120 is performing an ophthalmic surgery on an eye 104 of a patient 130 using a surgical tool 122. In FIG. 1, the eye 104 has been exposed using a speculum 140 and a contact lens 150 is held in place on the eye 104 and visually aligned with a surgical microscope 102 to facilitate visualization of inner structures of the eye 104. The surgeon 120 is using the surgical tool 122 to perform surgery on inner structures of the eye 104.

For example, when the surgical tool 122 is a vitrectomy probe, then the surgeon 120 may be using the surgical tool 122 to remove the clear, gel-like vitreous that normally fills the interior of the eye 104, taking care to remove substantially only the vitreous, while avoiding interaction with nearby eye structures, such as the retina, that are extremely sensitive to any mechanical action. The ability of the surgeon to clearly view the fundus is facilitated by a homogenous illumination field that is provided by illumination assembly 100. It is noted that surgical tool 122 may by any of a variety of handheld surgical tools. In some embodiments, illumination assembly 100 may be integrated within surgical tool 122 to provide illumination without having to use a secondary illumination tool.

In the inset of FIG. 1, additional details of the eye 104 during surgery are shown. Two scleral ports 108 for providing cannulated scleral penetration are visible, one for surgical tool 122 and one for illuminator assembly 100. As shown, illuminator assembly 100 may include focusing optics for mixed mode surgical laser illumination, as described in further detail below. Accordingly, illuminator assembly 100 may be used to project coherent light into the eye 104 using an optical fiber to transmit the light to project a homogenous illumination field (not visible in FIG. 1) into the fundus.

Modifications, additions, or omissions may be made to illuminator assembly 100 without departing from the scope of the disclosure. The components and elements of surgical illuminator assembly 100, as described herein, may be integrated or separated according to particular applications. Illuminator assembly 100 may be implemented using more, fewer, or different components in some embodiments.

Figure 2:
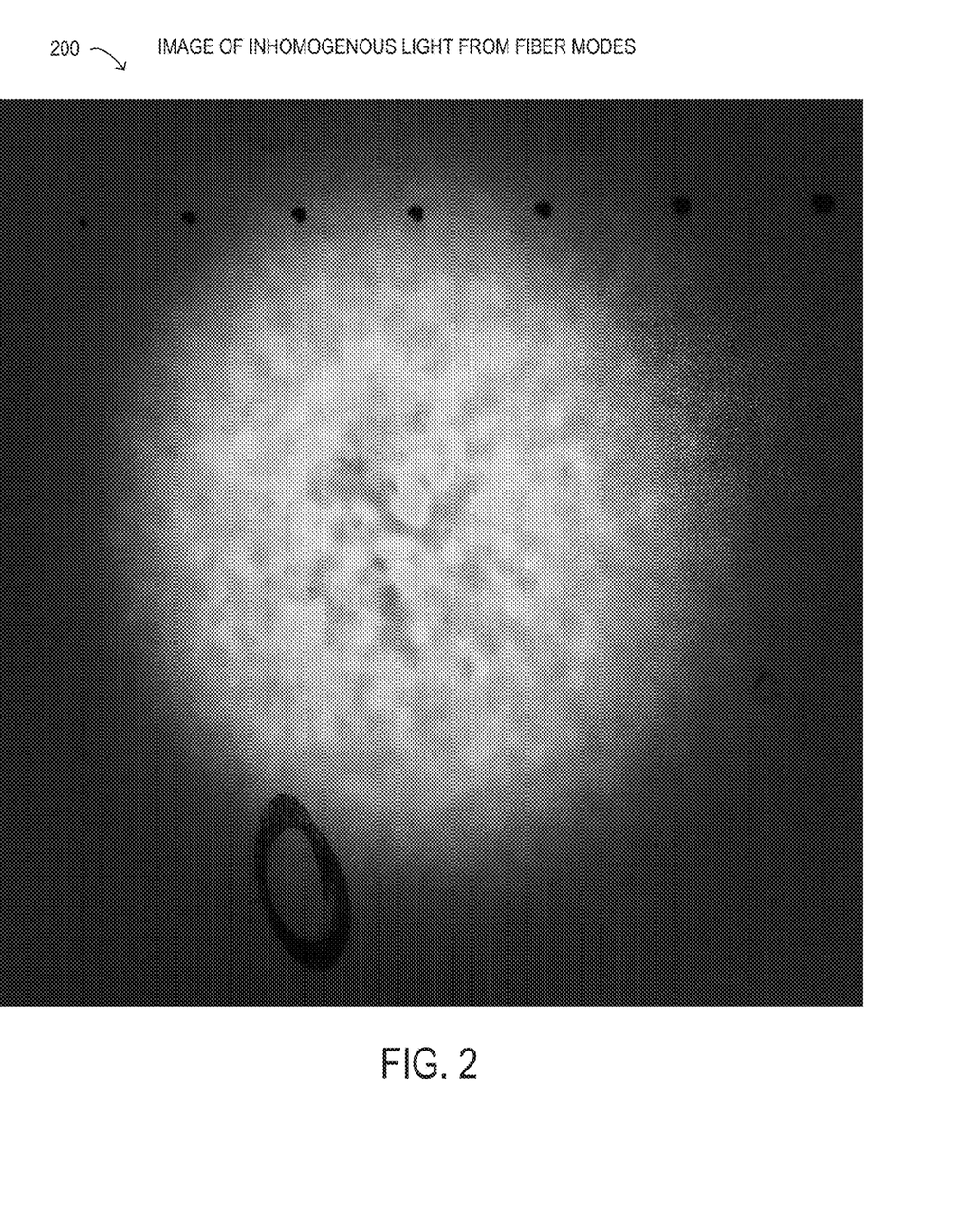
FIG. 2 is an image of inhomogeneous light from fiber modes.

FIG. 2 illustrates an image 200 of inhomogeneous light from fiber modes. Image 200 depicts coherent light from an optical fiber projected onto a screen that is oriented oblique to the page. In image 200, the depicted screen has extraneous annotations written in black ink above and below an inhomogeneous illumination field. The inhomogeneous illumination field in image 200 results from insufficient mode mixing within the optical fiber. The inhomogeneous illumination field in image 200 may exhibit intensity variations up to about 500%, which may be dynamic in many applications and usage scenarios, which is undesirable for surgical illumination, as explained previously. The inhomogeneous illumination field in image 200 may be immediately converted into a homogeneous illumination field, such as a substantially uniform intensity illumination field (not shown) by applying the techniques for mode mixing disclosed herein.

Figure 3:
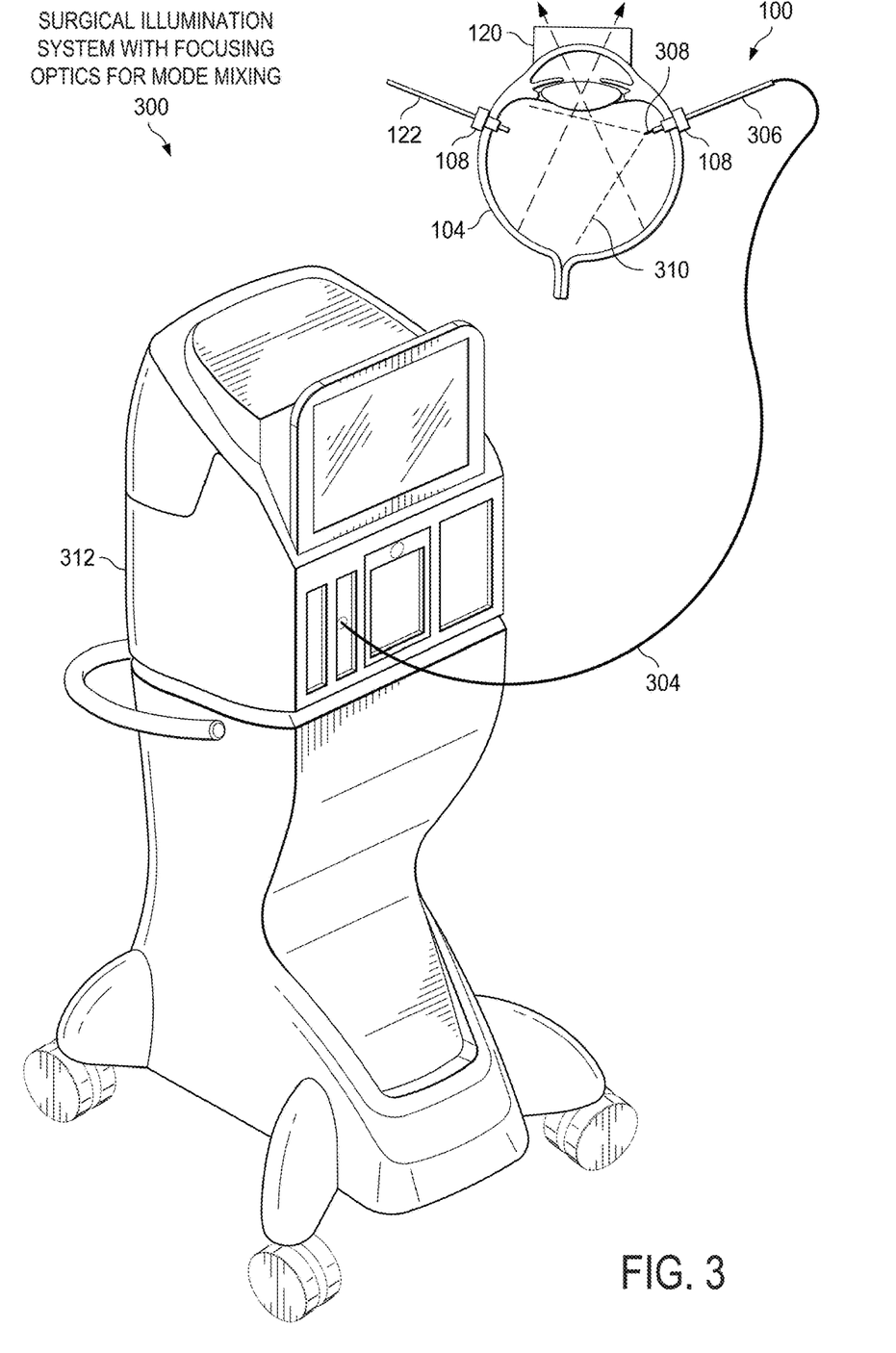
FIG. 3 is a depiction of an embodiment of a surgical illumination system with focusing optics for mode mixing.

Referring now to FIG. 3, a depiction of an embodiment of a surgical illumination system 300 is shown. As shown in FIG. 3, surgical illumination system 300 may be used in the ophthalmic surgery on the eye 104 shown in FIG. 1. FIG. 3 is a schematic illustration and is not drawn to scale or perspective. In FIG. 3, a cross-sectional view of the eye 104 is shown, enabling a view of various elements described above with respect to FIG. 1. Specifically, contact lens 120 is shown providing a relatively wide angle view of the fundus of the eye 104, while two scleral ports 108 penetrate the sclera of the eye 104. A surgical tool 122 is shown penetrating one scleral port 108, while illumination assembly penetrates another scleral port 108.

As shown in FIG. 3, a homogeneous illumination field 310 is projected into the eye 104 by illuminator assembly 100. Specifically, illuminator assembly 100 terminates distally with an optical fiber portion 308, which may be exposed to project light into the eye. Optical fiber portion 308 is coupled to an external optical fiber 304. In some embodiments, optical fiber portion 308 may be a distal portion of external optical fiber 304 itself. Optical fiber 304 is shown passing through a hand piece 306, which may include a sheath or tube around optical fiber 304 to enable cannulation at scleral port 108. Optical fiber 304 is shown extending from a surgical console 312 to hand piece 306.

In FIG. 3, surgical console 312 may include focusing optics for mixed mode surgical laser illumination, as disclosed herein. In some embodiments, the focusing optics for mixed mode surgical laser illumination may be implemented as a separate device (see FIGS. 4B and 4C). Specifically, surgical console 312 may include a focusing optic light source (see also FIG. 4A) comprised of a laser source and a condenser lens (or equivalent optical element). The condenser lens may focus first light generated by the laser source onto a focal spot at a fiber core of optical fiber 304 at a proximal end. Additionally, surgical console 312 may include a vibration stage for vibrating the condenser lens in a plane perpendicular to a transmission direction of optical fiber 304. In this manner, the focal spot is moved over the fiber core to generate second light that is transmitted by optical fiber 304. Because movement of the focal spot creates or enhances mode mixing in optical fiber 304, the second light may provide a homogeneous illumination field 310 in the eye 104 after exiting optical fiber portion 308, which is at a distal end of optical fiber 304.

Surgical console 312 may provide various other equipment and functionality, such as driver equipment for surgical tool 122, and a user interface for data operations and image processing. Further internal details of the focusing optics for mixed mode surgical laser illumination are described below with respect to FIGS. 4A, 4B, and 4C.

Figure 4A:
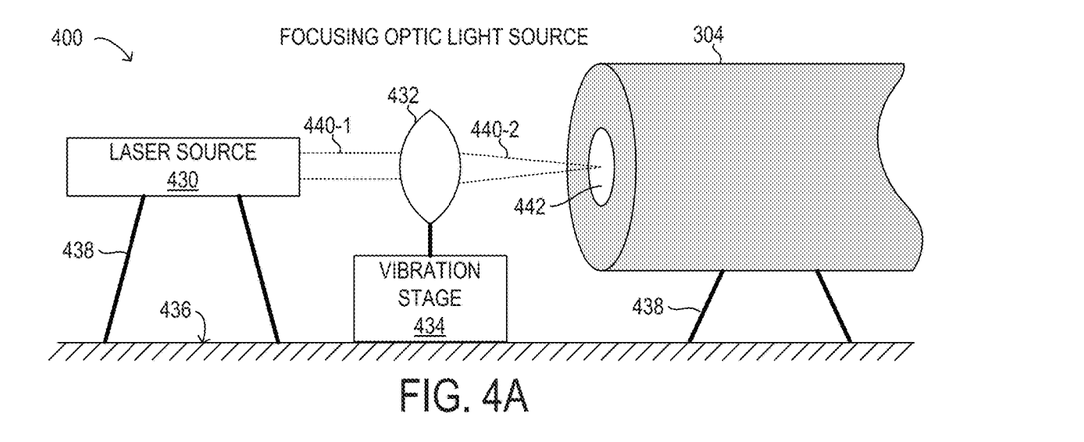
FIG. 4A is a depiction of an embodiment of a focusing optic light source.

Referring now to FIG. 4A, a depiction of an embodiment of a focusing optic light source 400 is shown. FIG. 4A is a schematic illustration and is not drawn to scale or perspective. In FIG. 4A, elements included within focusing optic light source 400 are shown schematically. It will be understood that focusing optic light source 400 may be implemented as an optical device, for example having an enclosure (not shown) to house the components illustrated in FIG. 4A. In particular embodiments, focusing optic light source 400 may be included with or integrated with surgical console 312 (see FIG. 3), where optical fiber 304 may begin at a distal end.

In focusing optic light source 400, a laser source 430 may represent a source of coherent light. Laser source 430 may represent a monochromatic light source. Laser source 430 may represent a combination of a plurality of monochromatic light sources, in some embodiments. Laser source 430 may generate first light 440-1, which is coherent light. First light 440-1 may be projected onto a condenser lens 432, which may be used to focus first light 440-1 onto a fiber core 442 of optical fiber 304 to generate second light 440-2. First light 440-1 may be generated as a collimated laser beam of about 1-5 mm in diameter having an optical power in the range of about 10-500 mW in various embodiments. First light 440-1 may be focused onto a focal spot that is about 5-10 µm in diameter by condenser lens 432. The focal spot may be less than 20 µm in diameter, or less than 25 µm in diameter in various embodiments. Fiber core 442 may be as small as about 30 µm in diameter. In some embodiments, fiber core 442 may about 50 µm in diameter, or about 100 µm in diameter, or various diameter sizes therebetween.

Additionally, in focusing optic light source 400, laser source 430, optical fiber 304, and a vibration stage 434 are shown situated on a fixed surface 436, which may represent a base of a housing (not shown) which may enclose focusing optic light source 400. In some embodiments, fixed surface 436 is included in surgical console 312. Laser source 430 and optical fiber 304 are fixed by supports 438, which may represent any type of mechanical attachment to hold laser source 430 and optical fiber 304 in a fixed position relative to condenser lens 432, as depicted.

As shown in FIG. 4A, vibration stage 434 may include mechanical components for moving or vibrating condenser lens 432, to which vibration stage 434 is fixed. The mechanical components may include any of a variety of mechanical actuators for generating motion of condenser lens 432, and thereby imparting motion to the focal spot of second light 440-2 on fiber core 442. Examples of mechanical components or actuators included in vibration stage 434 may encompass rotating motors, linear motors, piezoelectric actuators, pneumatic actuators, hydraulic actuators, electromagnetic actuators, and mechatronic actuators, among various different combinations. Vibration stage 434 may enable vibration, rotation, translation, or a combination thereof. Accordingly, vibration stage 434 may impart at least one of a reciprocal motion and a circular motion to condenser lens 432. In some embodiments, vibration stage 434 may impart a randomized motion to condenser lens 432. In particular, the motion of condenser lens 432 may be limited to a plane perpendicular to the page of FIG. 4A, to maintain a constant focal length to fiber core 442 that keeps the focal spot a fixed size. In some embodiments, the motion of condenser lens 432 may be along a transmission direction of optical fiber 304 (defocus mode), for example, when condenser lens 432 is an electronically tunable focusing lens. In different embodiments, vibration stage 434 may reciprocate, rotate, or oscillate at a frequency to cause motion that is not visible to the human eye, such as at a frequency of about 30 Hz or greater. Electromagnetic actuators may include various actuators with magnets or magnet windings (electromagnets) that are electronically controlled. Mechatronic actuators may include various combinations of electronic and mechanical systems or components, such as integrated robotic drives.

Although focusing optic light source 400 is described above with vibration stage 434 being mechanically coupled to condenser lens 432, it will be understood that the motion of second light 440-2 relative to fiber core 442 may be implemented as a relative motion for mode mixing purposes. Accordingly, in some embodiments, condenser lens 432 may be held fixed relative to surface 436, while optical fiber 304, or a connector in an optical path of optical fiber 304, may be coupled to vibration stage 434. In some embodiments, both condenser lens 434 and optical fiber 304, or the connector for optical fiber 304, may be mechanically coupled to a separate vibration stage, such as vibration stage 434.

Figure 4B:
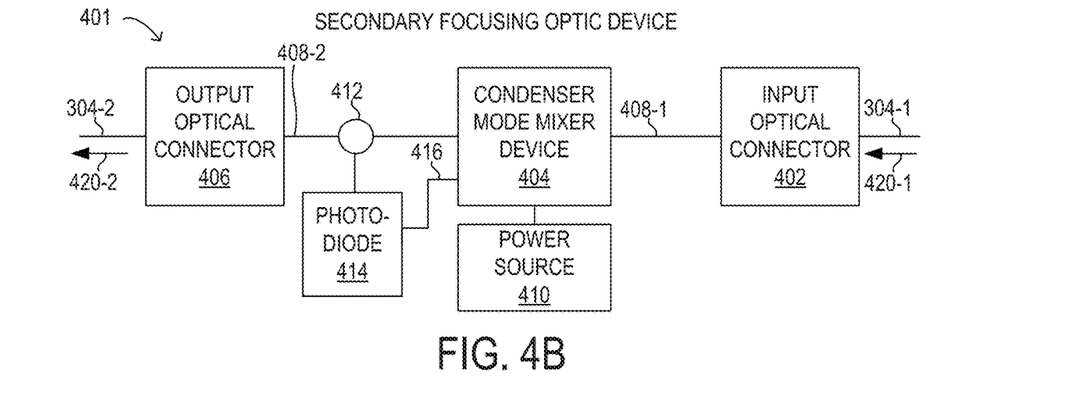
FIG. 4B is a depiction of an embodiment of a secondary focusing optic device.

Referring now to FIG. 4B, a depiction of an embodiment of a secondary focusing optic device 401 is shown. FIG. 4B is a schematic illustration and is not drawn to scale or perspective. In FIG. 4B, elements included within secondary focusing optic device 401 are shown schematically. It will be understood that secondary focusing optic device 401 may be implemented as an optical device, for example having an enclosure (not shown) to house the components illustrated in FIG. 4B. In particular embodiments, secondary focusing optic device 401 may be installed along optical fiber 304 as an intermediate optical device, while optical fiber 304 may be implemented in two sections with the appropriate optical connectors.

Specifically, secondary focusing optic device 401 is shown having input optical connector 402 for connecting to optical fiber 304-1, as well as having output optical connector 406 for connecting to optical fiber 304-2. In various embodiments, input optical connector 402 and output optical connector 406 may be releasable connectors (not shown) that mate with corresponding connectors attached to optical fibers 304-1 and 304-2. In some embodiments, input optical connector 402 and output optical connector 406 may be fixed connectors. As shown, input optical connector 402 couples to a first internal optical fiber 408-1 that connects to a condenser mode mixer device 404. Condenser mode mixer device 404 may connect to output optical connector 406 using a second internal optical fiber 408-2.

In secondary focusing optic device 401, input optical connector 402 may receive first light 420-1, which may experience insufficient mode mixing in optical fiber 304-1 after being transmitted from a coherent light source. The coherent light source may be a monochromatic laser, or a combination of monochromatic lasers that have been combined to generate first light 420-1. Accordingly, first light 420-1 may include light from different frequencies (i.e., colors). First light 420-1 is transmitted by first internal optical fiber 408-1 to condenser mode mixer device 404, which is similar to focusing optic light source 400, and is described in further detail below with respect to FIG. 4C. Condenser mode mixer device 404 may output second light 420-2 that has been mode mixed to second internal optical fiber 408-2, which connects to output optical connector 406.

As shown in FIG. 4B, an optical tap 412 may be used along second internal optical fiber 408-2 to divert some optical energy from second light 420-2 to a photodiode 414 (or another optical intensity sensor). A feedback control signal 416 from photodiode 414 may be used by condenser mode mixer device 404 to regulate the vibration of condenser lens 432 (included within condenser mode mixer device 404), such that the focal spot of condenser lens 432 remains directed at fiber core 442. When the focal spot of condenser lens 432 is not directed at fiber core 442, the intensity measured by photodiode 414 will decrease (assuming constant optical power at the coherent light source). In this manner, feedback control signal 416 may enable regulation of the motion of condenser lens 432 in a desired manner.

Also shown with secondary focusing optic device 401 in FIG. 4B is power source 410, which may provide power to vibration stage 434 included with focusing optic light source 400. In some embodiments, power source 410 may represent an internal power source to secondary focusing optic device 401, such as a battery to enable remote operation. In other embodiments, power source 410 may represent an external power source, such as a connector for line power or direct current from an external power supply (not shown).

Figure 4C:
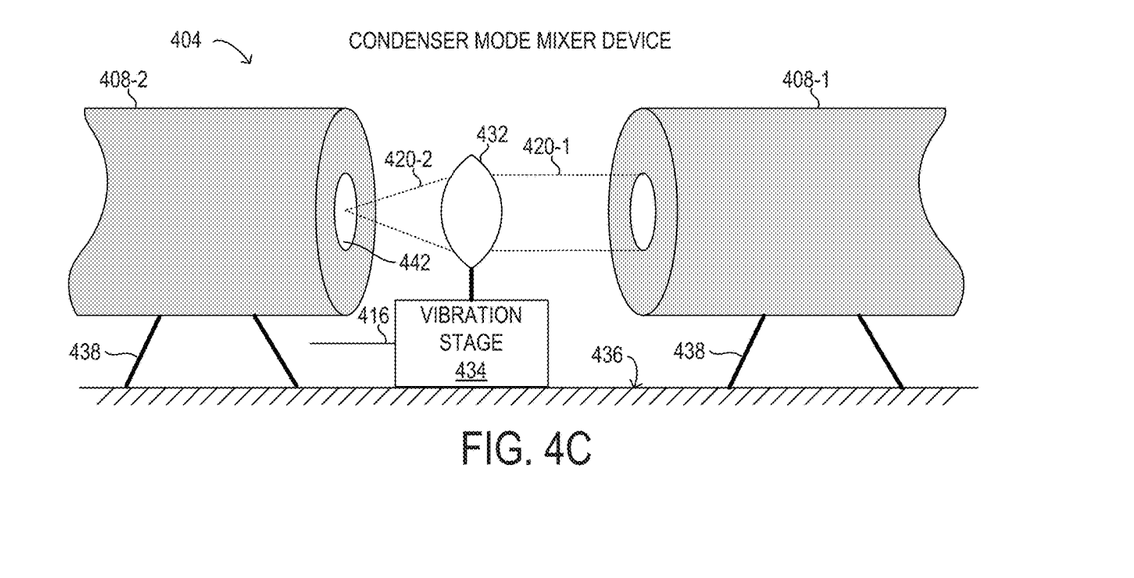
FIG. 4C is a depiction of an embodiment of a condenser mode mixer device.

Referring now to FIG. 4C, a depiction of an embodiment of condenser mode mixer device 404 (see also FIG. 4B) is shown. FIG. 4C is a schematic illustration and is not drawn to scale or perspective. In FIG. 4C, elements included within condenser mode mixer device 404 are shown schematically. It will be understood that condenser mode mixer device 404 may be implemented as an optical device, for example having an enclosure (not shown) to house the components illustrated in FIG. 4C. In particular embodiments, condenser mode mixer device 404 may be included with secondary focusing optic device 401 described above. As shown, first internal optical fiber 408-1, second internal optical fiber 408-2, and vibration stage 434 are situated on a fixed surface 436, which may represent a base of a housing (not shown) which may enclose condenser mode mixer device 404. First internal optical fiber 408-1 and second internal optical fiber 408-2 are fixed by supports 438, which may represent any type of mechanical attachment to hold optical fibers 408 in a fixed position relative to condenser lens 432, as depicted.

In condenser mode mixer device 404, first light 420-1 arrives from first internal optical fiber 408-1, as described previously. First light 420-1 may be projected onto condenser lens 432, which may be used to focus first light 420-1 onto a fiber core 442 of second internal optical fiber 408-2 to generate second light 420-2. Vibration stage 434 may operate to impart vibration, motion, rotation, or translation to condenser lens 432, as described previously. Vibration stage 434 is shown receiving feedback control signal 416 as an input for regulation of the motion of condenser lens 432, as described previously.

Although condenser mode mixer device 404 is described above with vibration stage 434 being mechanically coupled to condenser lens 432, it will be understood that the motion of second light 420-2 relative to fiber core 442 may be implemented as a relative motion for mode mixing purposes. Accordingly, in some embodiments, condenser lens 432 may be held fixed relative to surface 436, while optical fiber 408-2, or output optical connector 406, may be coupled to vibration stage 434. In some embodiments, both condenser lens 434 and optical fiber 408-2 or output optical connector 406, may be mechanically coupled to a separate vibration stage, such as vibration stage 434.

Figure 5:
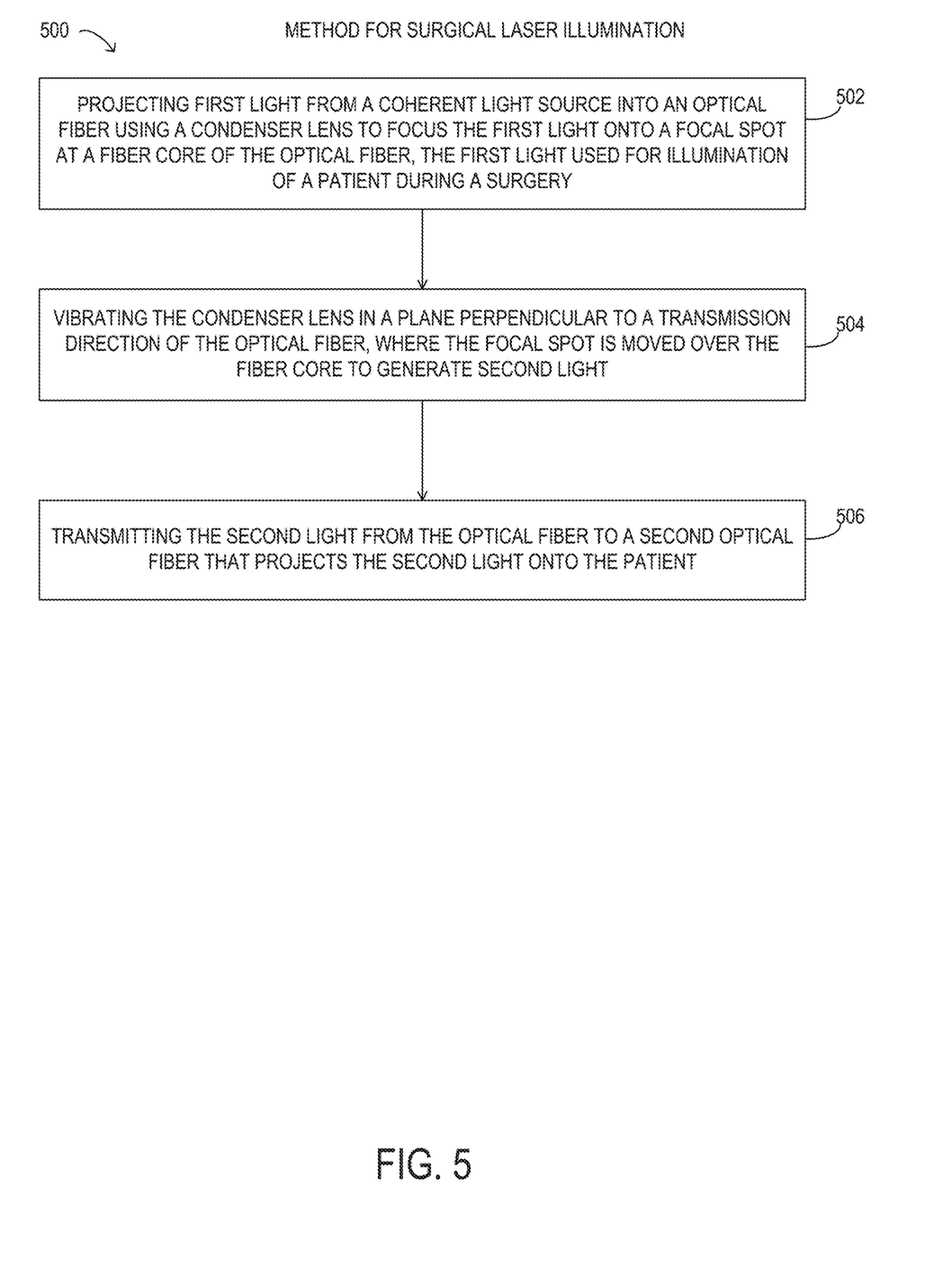
FIG. 5 is a flow chart of selected elements of a method for surgical laser illumination.

Referring now to FIG. 5, a flow chart of selected elements of an embodiment of a method 500 for surgical laser illumination using focusing optics for mode mixing, as described herein, is depicted in flowchart form. It is noted that certain operations described in method 500 may be optional or may be rearranged in different embodiments. Method 500 may be performed using illumination assembly 100, along with focusing optic light source 400 or secondary focusing optic device 402, as described herein.

Method 500 may begin, at step 502, by projecting first light from a coherent light source into an optical fiber using a condenser lens to focus the first light onto a focal spot at a fiber core of the optical fiber, the first light used for illumination of a patient during a surgery. At step 504, the condenser lens is vibrated in a plane perpendicular to a transmission direction of the optical fiber, where the focal spot is moved over the fiber core to generate second light. At step 506, the second light is transmitted from the optical fiber to a second optical fiber that projects the second light onto the patient.

As disclosed herein, focusing optics for mode mixing may be used to homogenize different modes in an optical fiber used for surgical illumination. A vibration stage may impart mechanical motion to a condenser lens to generate a homogeneous illumination field from a coherent light source.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A device for surgical illumination, the device comprising:
   a coherent light source for generating first light for illumination of a patient during a surgery;
   a condenser lens for focusing the first light onto a focal spot at a fiber core of a first optical fiber;
   a vibration stage for vibrating the condenser lens in a plane perpendicular to a transmission direction of the first optical fiber, wherein the focal spot is moved over the fiber core to generate second light; and
   a second optical fiber receiving the second light from the first optical fiber;
   wherein the surgery is an ophthalmic surgery, and the second optical fiber projects the second light into an eye of the patient, and further comprising:
   an optical intensity sensor to measure an intensity of the second light from the first optical fiber, wherein the vibration stage is controlled based on the intensity measured to limit movement of the focal spot to the fiber core.

2. The device of claim 1, wherein the coherent light source is a monochromatic laser.

3. The device of claim 1, wherein the coherent light source is a plurality of monochromatic lasers combined to generate the first light.

4. The device of claim 1, wherein the vibration stage further comprises:
   a piezoelectric actuator mechanically coupled to the condenser lens.

5. The device of claim 1, wherein the vibration stage further comprises:
   an electromagnetic actuator mechanically coupled to the condenser lens.

6. The device of claim 1, wherein the vibration stage further comprises:
   a mechatronic actuator mechanically coupled to the condenser lens.

7. The device of claim 1, wherein the vibration stage causes the condenser lens to impart at least one of a reciprocal motion and a circular motion to the focal spot.

8. The device of claim 1, wherein the condenser lens imparts a randomized motion to the focal spot.

9. A device for surgical illumination, the device comprising:
- a coherent light source for generating first light for illumination of a patient during a surgery;
- a condenser lens for focusing the first light onto a focal spot at a fiber core of a first optical fiber;
- a vibration stage for vibrating the condenser lens in a plane perpendicular to a transmission direction of the first optical fiber, wherein the focal spot is moved over the fiber core to generate second light and
- a second optical fiber receiving the second light from the first optical fiber;
- wherein the coherent light source is a third optical fiber receiving the first light from the coherent light source, and wherein the vibration stage and the condenser lens are included in a condenser mode mixer device further comprising:
- an input optical connector for connection to the third optical fiber;
- an output optical connector for connection to the second optical fiber; and
- a power source to power the vibrating of the condenser lens, wherein the condenser lens vibrates at a frequency greater than 30 Hz.

10. The device of claim 9, wherein the coherent light source is a monochromatic laser.

11. The device of claim 9, wherein the coherent light source is a plurality of monochromatic lasers combined to generate the first light.

12. The device of claim 9, wherein the vibration stage further comprises:
- a piezoelectric actuator mechanically coupled to the condenser lens.

13. The device of claim 9, wherein the vibration stage further comprises:
- an electromagnetic actuator mechanically coupled to the condenser lens.

14. The device of claim 9, wherein the vibration stage further comprises:
- a mechatronic actuator mechanically coupled to the condenser lens.

15. The device of claim 9, wherein the vibration stage causes the condenser lens to impart at least one of a reciprocal motion and a circular motion to the focal spot.

16. The device of claim 9, wherein the condenser lens imparts a randomized motion to the focal spot.

* * * * *